United States Patent
Busch et al.

(10) Patent No.: US 6,591,134 B2
(45) Date of Patent: Jul. 8, 2003

(54) IMPLANTABLE MEDICAL DEVICE

(75) Inventors: Ulrich Busch, Berlin (DE); Gregor Niewalda, Erlangen (DE)

(73) Assignee: Biotronik Mess-Und Therapiegerate GmbH & Co. Ingenieurburo Berlin, Berlin (DE)

( * ) Notice: Subject to any disclaimer, the term of this patent is extended or adjusted under 35 U.S.C. 154(b) by 282 days.

(21) Appl. No.: 09/768,794

(22) Filed: Jan. 25, 2001

(65) Prior Publication Data

US 2001/0025188 A1 Sep. 27, 2001

(30) Foreign Application Priority Data

Jan. 25, 2000 (DE) .......................... 100 02 932

(51) Int. Cl.[7] ............................ A61N 1/18; A61N 1/372
(52) U.S. Cl. ...................... 607/4; 607/5; 607/9; 607/32
(58) Field of Search ................ 607/4, 5, 7, 9, 607/30, 32, 60; 128/903

(56) References Cited

U.S. PATENT DOCUMENTS

| | | | | |
|---|---|---|---|---|
| 5,292,348 A | * | 3/1994 | Saumarez et al. ............. | 607/5 |
| 5,350,407 A | * | 9/1994 | McClure et al. .............. | 607/16 |
| 5,701,894 A | * | 12/1997 | Cherry et al. ................ | 600/300 |
| 5,883,397 A | | 3/1999 | Isoda et al. | |
| 5,935,154 A | | 8/1999 | Westlund | |
| 5,941,906 A | | 8/1999 | Barreras, Sr. et al. | |
| 5,954,666 A | * | 9/1999 | Snell ........................... | 607/32 |
| 6,021,393 A | * | 2/2000 | Honda et al. .................. | 705/3 |

FOREIGN PATENT DOCUMENTS

| | | |
|---|---|---|
| DE | 44 35 602 | 4/1996 |
| WO | 99 64106 | 12/1999 |

OTHER PUBLICATIONS

Drury et al., "Low–cost all–polymer integrated circuits", *Applied Physics Letters*. (1998), vol. 73, No. 1, pp. 108–110.
Dr. Wolfgang Stieler, "From the test tube", "Aus dem Reagenzias" (1999), Heft 2.

* cited by examiner

Primary Examiner—Willis R. Wolfe
(74) Attorney, Agent, or Firm—Browdy and Neimark, P.L.L.C.

(57) ABSTRACT

An implantable medical device incorporates
  a central control unit (14) for controlling the internal and external functions of the device,
  a memory unit comprising program memory, main and/or data memory (20, 21, 22) for the central control unit (14), having at least one non-volatile read-write memory unit that is based on an optical storage medium and holds the stored information energy-free, and
  an off-the-line power supply (18) for the implantable device.

5 Claims, 1 Drawing Sheet

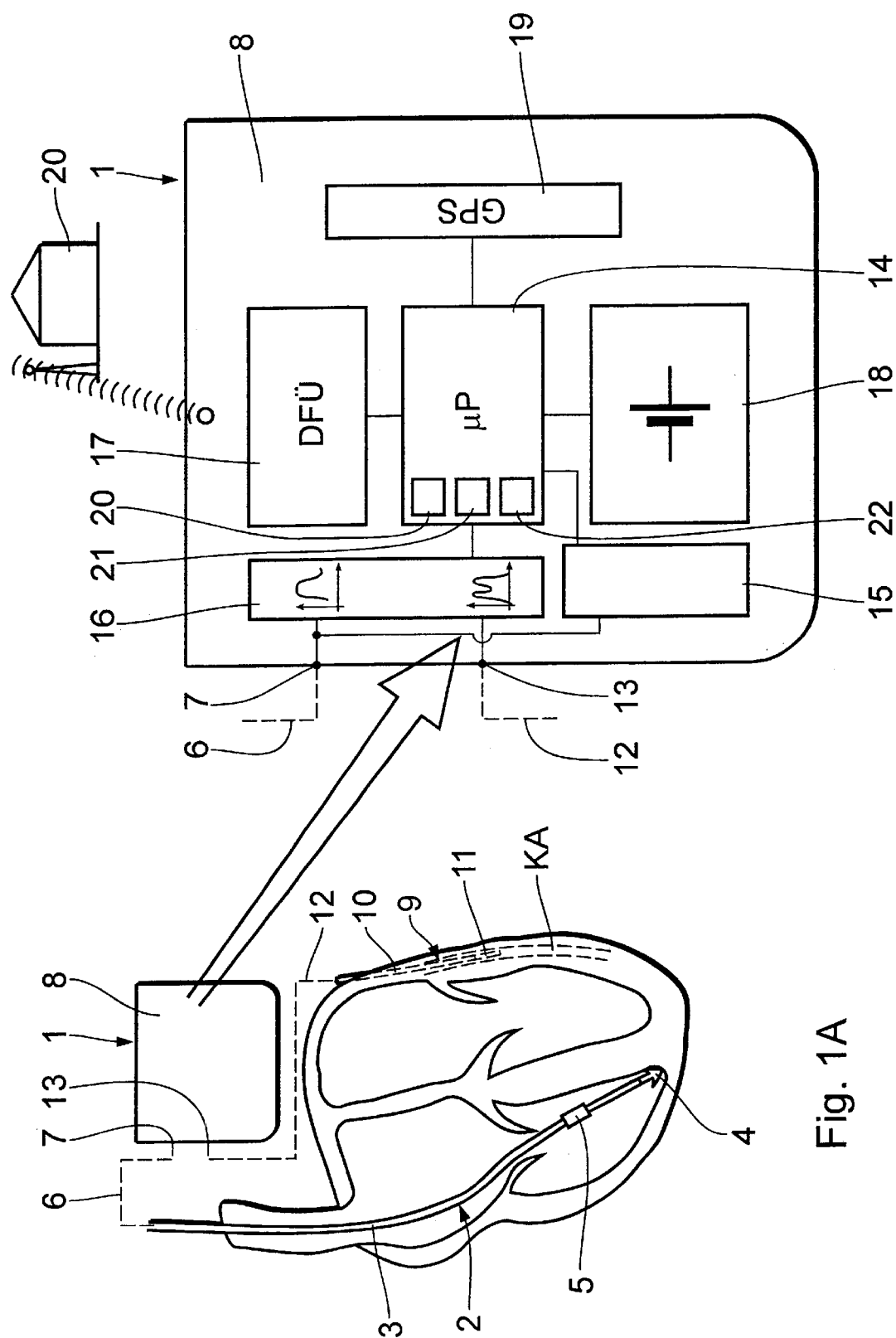

IMPLANTABLE MEDICAL DEVICE

BACKGROUND OF THE INVENTION

1. Field of the Invention

The present invention relates to an implantable medical device, more particularly an implantable cardiac device, such as a cardiac pacemaker or defibrillator.

2. Background Art

Implantable devices of this type generally incorporate a central control unit for controlling the internal and external functions of the device. In concrete terms for a cardiac pacemaker this means that a microprocessor, for example, assumes the internal pacemaker control processes, the processing of the EKG data obtained from measuring electrodes in the heart and the control of driver units for the delivery of electrical stimulation pulses to the heart.

To perform these functions, the central control unit requires, among others, a memory unit comprising program memory, main memory and/or data memory. The design of and need for the different types of memory depends on the functions of the implant.

Lastly, based on the nature of the location where these types of implantable devices are used, an off-the-line power supply must be provided for them, e.g., in the form of a battery.

A central problem with conventional implantable devices as they have been used until now, is the fact that semiconductor memory chips are used as the memory units. It is true that these semiconductor memory chips in themselves provide sufficient storage capacity to support also complex functions of the implantable devices. However, memory chips of this type also have a considerable current consumption, which, in practice, for devices that need to be implanted for the long term, limits the size of the memory chips that can be used. This, in turn, limits the functionality of the device, which, of course, counteracts the development trends towards an increasingly complex spectrum of functions for this type of implant. Furthermore, while semiconductor memories on the basis of submicron technologies, which are increasingly gaining importance, do require less and less space, their statistical power consumption, on the other hand, is growing superproportionally.

It is true that storage media are basically known from the prior art that operate based on magnetic effects virtually without power consumption and that can, therefore, be considered non-volatile storage. However, these have proven to be of little use for the relevant implantable devices because of their limited storage capacity, which is caused by other reasons.

SUMMARY OF THE INVENTION

It is an object of the invention to provide for an implantable medial device comprising a memory with low power consumption and high storage capacity.

To achieve this object, the present invention now proposes to use non-volatile read-write memories for the memory unit that are based on an optical storage medium and maintain the stored information energy-free.

This type of memory has significant advantages, particularly in view of its application in implantable devices that need to be operated off-the-line.

Energy is consumed merely for reading or changing the memory contents, but not for maintaining the information. This drastically reduces the energy consumption of an implant of this type so that, conversely, at a given pre-defined energy capacity, the storage capacity can be increased. Furthermore, optical memories may be implemented in very different configurations, which may be specifically tailored to their application in implantable medical devices. This variability does not exist to this extent in the silicon memory technology.

According to a first preferred variation for the optical storage medium, the latter may be a polymer with optically excitable molecule structures. The function of a memory cell is thus based, for example, on the orientation of a molecule in the polymer material, which is changeable by emitting light onto the memory medium. The given orientation may be reflected in optical properties, such as, e.g., the polarity or the absorption coefficient of the material. It is via these physical properties that the information can be scanned from outside. The writing and reading of information may take place especially by means of emitting different optical pulses onto the memory medium. Pulses below the limit value, for example, may be used to scan the absorption coefficient of an optical memory cell and thus their information contents. If an optical pulse above the defined limit value is emitted onto the memory medium, the molecule structure is excitable and can accept a new information content, e.g., in the form of a changed absorption coefficient, through a change in its orientation.

The control circuit of a polymeric read-write memory of this type may be advantageously implemented with polymeric transistors in such a way that the interface between the silicon based functional blocks of the implant and the optical memory unit may be reduced to a few contacts.

As a second preferred alternative for an optical storage medium, the invention comprises a semiconductor material with optically excitable energy sinks in a conductance band. According to this concept, electrons can first be raised into the conductance band by means of optical excitation processes, where they are maintained energy-free by the energy sinks. A memory cell can thus be implemented in this manner as well, in such a way that the scanning of the information and raising of the electrons into the conductance band and, vice versa, its inverse transformation to the initial state, again takes place via the emittance of light of a certain wavelength onto the memory medium.

Further characteristics, details and advantages of the invention will become apparent from the following description, in which an embodiment will be explained in greater detail based on the appended drawing.

BRIEF DESCRIPTION OF THE DRAWING

FIGS. 1A and 1B show a schematic illustration, partly in the form of a block diagram, of an implantable detection device for the detection of ischaemia conditions of the heart.

DESCRIPTION OF THE PREFERRED EMBODIMENT

Presented in FIGS. 1A and 1B is a schematic rendering of an implantable detection device, which has an implant casing 1 designed in the fashion of a pacemaker. This detection device is implanted into the thorax of a patient at risk of ischaemia. The detection device is furthermore provided with an electrode sensor array 2 comprising a catheter 3 having a stimulation electrode 4 for the delivery of a stimulation pulse to the heart and a unipolar, fractally coated pacemaker electrode as the sensor electrode 5 for the detection of, e.g., the ventricularly evoked response of the heart. The electrode sensor array 2 is connected, by an interconnection line 6 indicated by a dashed line, to the control unit 8 shown in the enlarged section of FIG. 1B via a corresponding input 7 on the implant casing 1.

Furthermore, a blood flow sensor arrangement 9 is provided, which, in the shown embodiment, comprises a catheter 10 that is inserted into a coronary artery KA and has a flow sensor 11, for example on the basis of an ultrasound-Doppler measuring head or an impedance measuring electrode. The blood flow sensor arrangement 9, too, is connected via an interconnecting line 12 to a corresponding input 13 of the control unit 8.

The control unit 8 incorporates, as the central control unit, a microprocessor 14, which controls all further components of the control unit 8 in the usual manner via an appropriate operating program. A program memory 20 for storing the operating program is assigned to the microprocessor 14. In the performance of all device internal control functions and the sequence control, a main memory 21 serves for the external functionalities of the interim storage of the respective working data. Furthermore, a data memory 22 is provided, which, for example, maintains certain programming settings for the detection device in the memory.

The memory units 20, 21 and 22 are designed as non-volatile read-write memories that are based on an optical storage medium and hold the stored information energy-free. The memories are designed as so-called "organic memories" that are based on a layered polymer material with optically excitable molecule structures. The basic design of memories of this type and their operation was already explained in the introductory part of the present description, to which reference is hereby made to avoid repetition. Further information regarding the state of the art of these memory units can furthermore be found in an article from the computer magazine c't, No. 3/1998, page 18, Ulrike Kuhlmann, Dr. Jürgen Rink "Terabytes in Plastik-folie— organische Massenspeicher vor der Serienproduktion?"

A battery 18 is provided for the energy supply to the internal units 14, 15, 16, 17 and 19 of the device, which have already been discussed and/or will be described in greater detail below.

Via the control unit 8, a stimulation device 15 is now activated in such a way that it activates a pulse through the stimulation electrode, for example for the generation of a ventricularly evoked response (VER).

The detection device 16 is provided for analyzing and forwarding the signals provided by the sensor arrays 2, 9 for the ventricularly evoked response and the blood flow measured in the coronary artery KA. For example, when the amplitude of the VER drops due to ischaemia and falls below a certain first threshold—i.e., when an acute ischaemia attack is not yet present—the command is given to a cardiac pacemaker, which may have as a component the inventive implantable detection device, to set an upper limit for the stimulation rate. This keeps the metabolism requirements of the myocardial tissue low, so that a further worsening of the ischaemic condition can be countered. In an ischaemia condition of this type, the blood flow sensor array 9 does not yet detect any significant lowering of the supply to the myocardium.

In case of a further drop in the amplitude of the VER below a second threshold and, optionally, when a reduction in the blood flow is measured in the coronary artery KA with the aid of the sensor array 9, emergency measures of varying degrees may now need to be initiated. For this purpose, the detection device is provided with a data link device 17 on the basis of the telemetry techniques commonly used in cardiac pacemaker technology, whereby signal data that are detected in the control unit 8 and evaluated and processed by the detection device 16, can be routed to an outside station or base station 20 not shown in detail, e.g., a cardiac center caring for the patient. From there, further measurements may be initiated, also via the data link device 17, for example with the aid of the detection device or with the aid of the cardiac pacemaker coupled to the same. The patient may furthermore be asked by the base station 20 to see his physician.

Furthermore, a navigational device 19 that is based on the customary GPS system or on a GSM system and coupled to the data link device 17 is integrated into the detection device. It can be used, particularly during an acute ischaemia attack, to determine the location of the patient and report this location to the base station 20. The base station 20 can then immediately notify emergency personnel who will know the patient's geographic location via the satellite navigational device. This ensures extremely quick emergency measures that are selectively adapted to the severity of the ischaemia attack.

What is claimed is:

1. An implantable medical device, more particularly an implantable cardiac device, such as a cardiac pacemaker or defibrillator, having a central control unit (14) for controlling internal and external functions of the device, a memory unit comprising at least one of program memory, main memory and data memory (20, 21, 22) for the central control unit (14), and an off-the-line power supply (18) for the implantable device, wherein the memory unit (20, 21, 22) incorporates at least one non-volatile read-write memory based on an optical storage medium and holding a stored information energy-free.

2. An implantable device according to claim 1, wherein the optical storage medium is a polymer with optically excitable molecule structures.

3. An implantable device according to claim 2, wherein the molecule structures of the optical storage medium are selectively readable or switchable for writing new information trough an emittance of various optical pulses onto the optical storage medium.

4. An implantable device according to claim 1, wherein a control circuit of the read-write memory is implemented on the basis of polymeric transistors.

5. An implantable device according to claim 1, wherein the optical storage medium is a semiconductor material with optically excitable energy sinks in a conductance band.

* * * * *